(12) United States Patent
Chari et al.

(10) Patent No.: US 11,401,301 B2
(45) Date of Patent: Aug. 2, 2022

(54) METHOD FOR THE PURIFICATION OF BIOLOGICAL MACROMOLECULAR COMPLEXES

(71) Applicant: MAX-PLANCK-GESELLSCHAFT ZUR FÖRDERUNG DER WISSENSCHAFTEN E.V., Munich (DE)

(72) Inventors: Ashwin Chari, Goettingen (DE); Holger Stark, Waake (DE); Jil Schrader, Goettingen (DE); Fabian Henneberg, Goettingen (DE)

(73) Assignee: Max-Planck-Gesellschaft zur Foerderung der Wissenschaften e.V., Munich (DE)

(*) Notice: Subject to any disclaimer, the term of this patent is extended or adjusted under 35 U.S.C. 154(b) by 121 days.

(21) Appl. No.: 17/060,627

(22) Filed: Oct. 1, 2020

(65) Prior Publication Data

US 2021/0017224 A1   Jan. 21, 2021

Related U.S. Application Data

(62) Division of application No. 16/307,200, filed as application No. PCT/EP2017/063638 on Jun. 6, 2017, now Pat. No. 10,829,515.

(30) Foreign Application Priority Data

Jun. 6, 2016 (EP) .................................... 16173037

(51) Int. Cl.
*C07K 1/36* (2006.01)
*C07K 1/30* (2006.01)
*C07K 1/32* (2006.01)

(52) U.S. Cl.
CPC .................. *C07K 1/36* (2013.01); *C07K 1/30* (2013.01); *C07K 1/306* (2013.01); *C07K 1/32* (2013.01); *C12Y 203/01085* (2013.01)

(58) Field of Classification Search
CPC . C07K 1/36; C07K 1/30; C07K 1/306; C07K 1/32; C12Y 203/01085
See application file for complete search history.

(56) References Cited

U.S. PATENT DOCUMENTS

| | | | |
|---|---|---|---|
| 6,773,894 B1* | 8/2004 | Han ..................... | G01N 33/567 436/536 |
| 2010/0239609 A1* | 9/2010 | Reiter ..................... | A61P 31/12 435/239 |
| 2017/0369528 A1* | 12/2017 | Nadgoud ................ | C07C 51/43 |

FOREIGN PATENT DOCUMENTS

| CN | 102666873 A | 9/2012 |
|---|---|---|
| JP | H05292964 A | 11/1993 |

(Continued)

OTHER PUBLICATIONS

Tanaka et. al. 1986 "A high molecular weight protease in the cytosol of rat liver" vol. 261, No. 32, Issue of Nov. 15, pp. 15197-15203 (Year: 1986).*

(Continued)

*Primary Examiner* — Liam Royce
(74) *Attorney, Agent, or Firm* — WCF IP

(57) ABSTRACT

The present invention relates in a first aspect to a method for the purification of biological macromolecular complexes. Typically, no chromatography steps are applied. That is, the present invention relates to a method for the purification of biological macromolecular complexes Furthermore, the present invention relates to a method for crystallization of biological macromolecular complexes comprising the step of purification as described followed by crystallization in a reservoir solution containing a water-soluble polymer. Fur- (Continued)

thermore, purified biological macromolecular complexes obtainable by the method according to the present invention are provided as well as crystallized biological macromolecular complexes. Finally, a method for determining the suitability of a candidate compound for inhibiting the 20S proteasome of an individual is provided. Said method is particularly useful in personalized medicine identifying suitable inhibitors of the 20S proteasome in individuals for treating, ameliorating or preventing a cancer, an autoimmune disease, a muscular dystrophy, emphysema or cachexia accompanying cancer or AIDS.

6 Claims, 4 Drawing Sheets

(56) References Cited

FOREIGN PATENT DOCUMENTS

| JP | H06022759 A | 2/1994 |
|---|---|---|
| JP | 2001269168 A | 10/2001 |
| JP | 2002293749 A | 10/2002 |
| JP | 2010180222 A | 8/2010 |
| JP | 2014532184 A | 12/2014 |
| WO | 2013/014186 A1 | 1/2013 |

OTHER PUBLICATIONS

Tanaka 2009. "The proteasome: overview of structure and functions" Proc. Jpn. Acad., Ser. B 85 (Year: 2009).*
Groll et. al. 2000. Crystal structure of epoxomicin:20S proteasome reveals a molecular basis for selectivity of α'β'-epoxyketone proteasome inhibitors. J. Am. Chem. Soc. 2000, 122, 1237-1238 (Year: 2000).*
Harshbarger et. al. 2015. "Crystal structure of the human 20s proteasome in complex with carfilzomib". Structure 23, 418-424 (Year: 2015).*
Kaneko et al: "Assembly Pathway of the Mammalian Proteasome Base Subcomplex Is Mediated by Multiple Specific Chaperones", Cell, vol. 137, pp. 914-925, May 29, 2009.

* cited by examiner

METHOD FOR THE PURIFICATION OF BIOLOGICAL MACROMOLECULAR COMPLEXES

The present invention relates in a first aspect to a method for the purification of biological macromolecular complexes. Typically, whereby no chromatography steps are applied. That is, the present invention relates to a method for the purification of biological macromolecular complexes comprising the steps of a) providing a crude sample containing the biological macromolecular complexes; b) conducting a first centrifugation step for separation of cell debris at 25.000 to 35.000×g; c) supplementing the supernatant obtained from the first centrifugation step with an osmolyte in an amount of from 0% to 25% (w/v) and compounds allowing thiol-alkylation of cysteines; d) conducting a second centrifugation step by centrifugation at 50.000 to 150.000×g, like 80.000 to 120.000×g; e) treating the supernatant obtained from the second centrifugation step with a water-soluble polymer, in particular, a non-ionic polymer or a polymer with zero net charge, like polyalkylene glycol, polyamine, or polycarboxylate for precipitation; f) conducting a density gradient centrifugation using an osmolyte with the polymer-based precipitate like the polyalkylene glycol-based precipitate, after resuspension thereof in a buffer not containing said polymer, like the polyalkylene glycol; g) optionally repeating once or multiple times step e) and f); h) concentration by water-soluble polymer based precipitation, like polyalkylene glycol based precipitation of the biological macromolecular complexes; for obtaining a purified biological macromolecular complexes.

Furthermore, the present invention relates to a method for crystallization of biological macromolecular complexes comprising the step of purification as described followed by crystallization in a reservoir solution containing a water-soluble polymer. Furthermore, purified biological macromolecular complexes obtainable by the method according to the present invention are provided as well as crystallized biological macromolecular complexes. Finally, a method for determining the suitability of a candidate compound for inhibiting the 20S proteasome including the immunoproteasome of an individual is provided. Said method is particularly useful in personalized medicine identifying suitable inhibitors of the 20S proteasome including the immunoproteasome in individuals for treating, ameliorating or preventing a cancer, an autoimmune disease, a muscular dystrophy, emphysema or cachexia accompanying cancer or AIDS.

PRIOR ART

For many biochemical needs it is desirable to be able to separate particular molecules from a mixture of molecules for further analysis. This includes for example the purification of proteins or other biomolecules from cell extracts; the purification of synthesized chemicals from contaminants or the separation of chemical mixtures, in particular biological macromolecular complexes. Macromolecular complexes, for example biological macromolecular complexes are supramolecular assemblies or identical moieties. For example, biological macromolecular complexes are assemblies of identical or different biomolecules even of different type of biomolecules. Such biomolecules include proteins, nucleic acids, lipids and sugars. Typically, the biological macromolecular complexes are formed under specific conditions present in the natural environment, like the living organism. Said biological macromolecular complexes are crucial for the survival of living organisms and have key functions in various biochemical pathways. A key to the mechanistic understanding how these biological macromolecular complexes conduct their tasks is the knowledge about their three-dimensional structure. However, one major obstacle of studying structures of biological macromolecular complexes, in particular, the function of said biological macromolecular complexes, is the compositional complexity thereof and, based thereon, often the relative instability of said structures, in particular, when being isolated from the natural environment. That is, the structure determination and correct formation in the macromolecular assembly is difficult to achieve during purification when expressed recombinantly or produced synthetically. In particular, when isolating and purifying the biological macromolecular complexes a goal is to provide the purified biological macromolecular complexes in a functional state and stable in structure. Ongoing research in the biological sciences reveals that macromolecules in general do not act in isolation but instead are organized into supramolecular assemblies. These modules called biological macromolecular complexes or molecular machines are the active species which perform biochemical reactions essential to maintain cellular homeostasis. Molecular machines or biological macromolecular complexes, in the following referred to as biological macromolecular complexes or, generally, as complexes can be divided into three major classes, those composed of protein only, those consisting of protein and nucleic acid as well as integral membrane complexes.

That is, to allow to determine the three-dimensional structure to gain mechanistic inside into the respective mode of action within cells, it is required to provide the biological macromolecular complexes stable and fully functional.

The growing sciences of proteomics requires the identification of molecules and larger assemblies of interacting molecules forming biological macromolecular complexes within a cell's proteome being the entirety of proteins produced by a particular cell at a particular time. Therefore, generic methods are needed that allow analysis of proteins whereby for studying mechanistic activities, the purification should allow to provide the biological macromolecular complexes with high purity and abundance.

For the mechanistic understanding of its cellular activities and its therapeutic targeting in disease, the illustration of higher resolution structures of the biological macromolecular complexes is of paramount importance.

Today various methods and tools are provided allowing purification of proteins and larger complexes. Most of these methods are based on chromatography steps using appropriate columns to allow purification. However, column or chromatography based purification is laborious and expensive. In addition, these types of purification methods do not represent a suitable method allowing simple and rapid purification of the desired functional biological macromolecular complexes accordingly. Suitable separation or purification methods include several different methods such as precipitation and dialysis techniques, chromatography methods and gel electrophoresis which make use of the separation of molecules according to their mobility which is dominated by their charge/mass ratio. Electrophoresis is widely used and is usually performed in a porous matrix, such as agarose or polyacrylamide gel. Often molecules are separated by application of an electric field in a first dimension relative to their mobility and, thereafter, to an electric field different in orientation from the electric field used for separation in the first dimension, thus, creating a two-dimensional gel electrophoresis. However, gel electrophoresis is not the method of choice for purification of functional macromolecules. That is, typically electrophoresis needs to provide denaturing conditions although native electrophoresis is possible. However, similar to the chromatographic isolation, electrophoresis is based on net charge despite the size due to the porous matrix.

Presently, the method of choice is the chromatographic isolation and purification. However, typically this kind of purification procedure results in macromolecules not suitable for further analysis, e.g. by crystallization.

Hwang K Y et al., Mol. And Cells. 1994, 4, 273-275 describe the crystallization of 20S proteasome from rat liver. US 2006/0281118 A1 describes methods and compositions for rapid purification of proteasomes and methods of use of components thereof. Evteeva I. N. et al., Citologica Nauka, St. Petersburg, Russland, 2013, 55 (12), 893-900 relates to a comparative analysis of methods for purification and concentration of 26S proteasomes isolated from rat liver. JP H05 292964 A describe a production method for purifying the human 26S proteasomes in stable state and the human 26S proteasome itself.

The methods described in the referenced documents typically contain purification based on gel filtration or other column and chromatography based methods.

In WO 2013/034160 methods are provided for analyzing biological macromolecular complexes based on determining the assembly, homogeneity and/or thermodynamic stability of said complexes accordingly. However, performing the method described therein requires the provision of purified macromolecular complexes accordingly.

Hence, there is an ongoing need for methods allowing rapid and simple purification of biological macromolecular complexes whereby these complexes maintain their activity and functionality.

BRIEF DESCRIPTION OF THE PRESENT INVENTION

In a first aspect, the present invention provides a method for the purification of biological macromolecular complexes comprising the steps of:
a) providing a crude sample containing the biological macromolecular complexes;
b) conducting a first centrifugation step for separation of cell debris at 25.000 to 35.000×g;
c) supplementing the supernatant obtained from the first centrifugation step containing an osmolyte in an amount of from 0% to 25% (w/v) and compounds allowing thiol-alkylation and/or reduction of cysteines;
d) conducting a second centrifugation step by centrifugation at 50.000 to 150.000×g, like 80.000 to 120.000×g;
e) treating the supernatant obtained from the second centrifugation step with a water-soluble polymer, in particular, a non-ionic polymer or a polymer with zero net charge, like polyalkylene glycol, polyamine, or polycarboxylate for precipitation;
f) conducting a density gradient centrifugation using an osmolyte with the polymer-based precipitate like the polyalkylene glycol-based precipitate, after resuspension thereof in a buffer not containing said polymer, like the polyalkylene glycol;
g) optionally repeating once or multiple times step e) and f)
h) concentration by water-soluble polymer based precipitation, like polyalkylene glycol based precipitation of the biological macromolecular complexes; for obtaining a purified biological macromolecular complexes.

In another aspect, the present invention provides a method for crystallization of biological macromolecular complexes comprising the method for the purification of biological macromolecular complexes according to a method according to the present invention further comprising the step of crystallization in a reservoir solution containing a water-soluble polymer, in particular, a non-ionic polymer or a polymer with zero net charge, like polyalkylene glycol amine, or polycarboxylate, in particular, polyethylene glycol.

Furthermore, the present invention provides a purified biological macromolecular complex obtainable by a method according to the present invention. These purified biological macromolecular complexes are suitable for further crystallization of said complexes beside its use for other mechanistic determination or functional analysis.

Moreover, the present invention relates to a crystallized biological macromolecular complex obtainable by a method according to the present invention.

Finally, the present invention provides a method for determining the suitability of a candidate compound for inhibiting the 20S proteasome including the immunoproteasome of an individual comprising the
steps of the method for crystallization of the 20S proteasome including the immunoproteasome of said individual containing the candidate compound according to the present invention or providing a crystallized 20S proteasome containing the candidate compound according to the present invention;
determining the crystal structure of the 20S proteasome including the immunoproteasome by diffraction analysis with resolution of 2.2 Å or below;
determining suitability of the candidate compound as an inhibitor of the 20S proteasome including the immunoproteasome of an individual based on said analysis.

BRIEF DESCRIPTION OF THE DRAWINGS

FIG. 1 shows a flowchart of the steps performed according to the present invention for purification of biological macromolecular complexes.

FIG. 2 shows a flowchart of the steps performed according to the present invention for purification of 20S proteasome.

FIG. 3 is a SDS page showing the purified protein as well as the purification thereof in different fractions and intermediate fractions obtained in the method according to the present invention. Aliquots of S30 (lane 2) and S100 (lane 3) extracts, the resuspended PEG cut (lane 4), the pool of the 1., and 2. sucrose gradients (lanes 5 and 6) as well as the final purified protein preparation (lane 7) and a molecular weight marker (lane 1) are depicted.

FIG. 4 shows a rotation photograph of human 20S proteasome crystals obtained by a method according to the present invention. Shown is a typical diffraction pattern of stabilized and dehydrated human 20S proteasome crystals measured by the oscillation method. The diffraction limit of this particular crystal is 1.8 Å.

DETAILED DESCRIPTION OF THE PRESENT INVENTION

Figure 1:
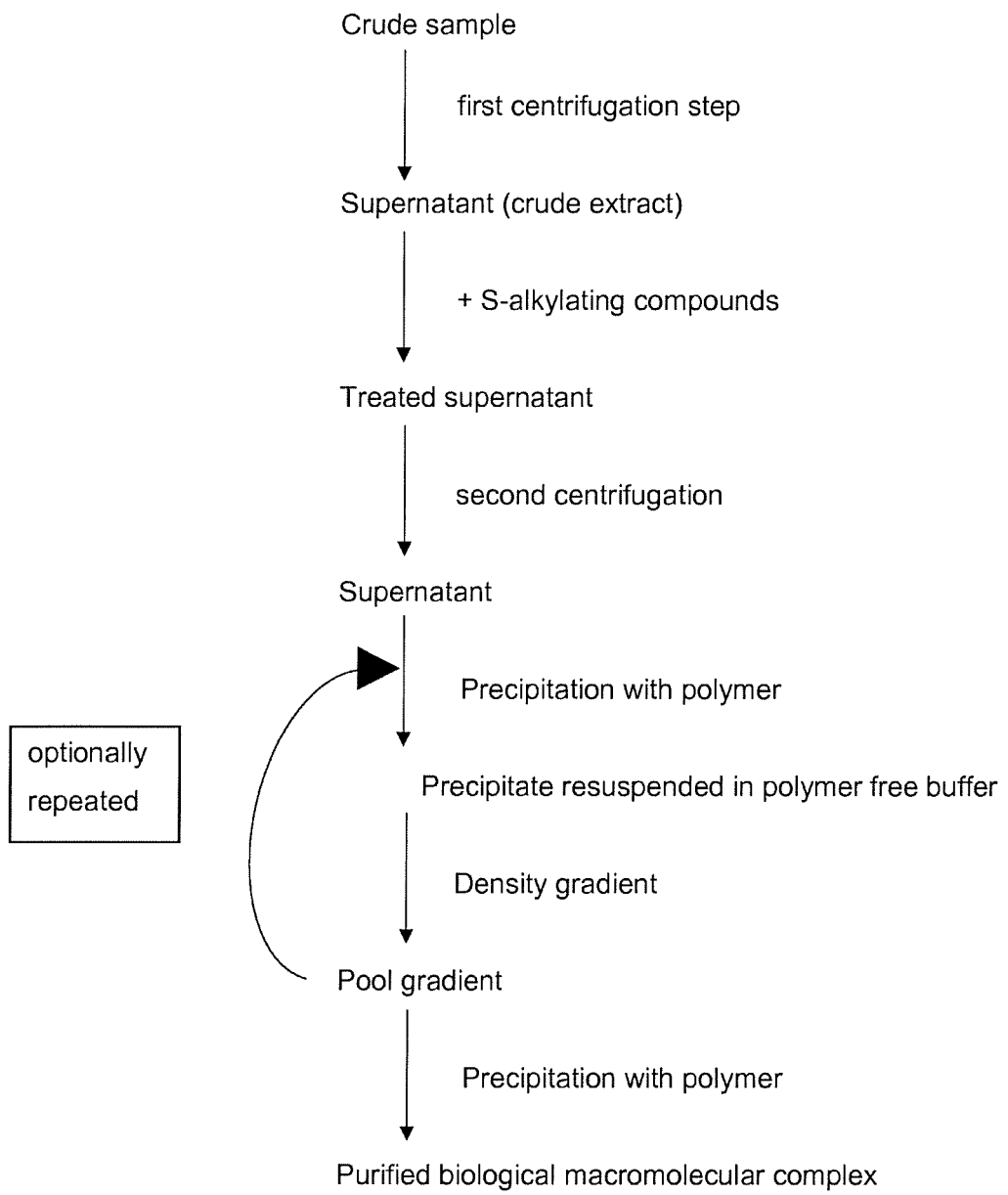
FIG. 1.

The present invention relates in a first aspect to a method for the purification of biological macromolecular complexes comprising the steps of:
a) providing a crude sample containing the biological macromolecular complexes;
b) conducting a first centrifugation step for separation of cell debris at 25.000 to 35.000×g;

c) supplementing the supernatant obtained from the first centrifugation step an osmolyte in an amount of from 0% to 25% (w/v) and compounds allowing thiol-alkylation of cysteines;

d) conducting a second centrifugation step by centrifugation at 50.000 to 150.000×g, like 80.000 to 120.000×g;

e) treating the supernatant obtained from the second centrifugation step with a water-soluble polymer, in particular, a non-ionic polymer or a polymer with zero net charge, like polyalkylene glycol, polyamine, or polycarboxylate for precipitation;

f) conducting a density gradient centrifugation using an osmolyte with the polymer-based precipitate like the polyalkylene glycol-based precipitate, after resuspension thereof in a buffer not containing said polymer, like the polyalkylene glycol;

g) optionally repeating once or multiple times step e) and f)

h) concentration by water-soluble polymer based precipitation, like polyalkylene glycol based precipitation of the biological macromolecular complexes;

for obtaining a purified biological macromolecular complexes.

Of note, some of the above steps may be in different order. For example, step c) may be conducted before step b) etc.

As used herein, the term "macromolecular complexes" and in particular, the term "biological macromolecular complexes" means, in accordance with the present invention, any assembly made up of subunits. The subunit usually is the smallest unit of the macromolecular complex and is the cause for the characteristic structure or property of the macromolecular complex. The subunit is, for example, a protein monomer, a DNA- or RNA-macromolecule. As mentioned, the macromolecular complexes are supramolecular assemblies of different or identical moieties or subunits. The complexes are usually composed of at least two identical or different subunits forming a macromolecular complex of a size of at least 500 kDa and larger. If many identical subunits associate to form the macromolecular complex, then one designates it as a homo-oligomeric macromolecular complex. A common example for a homo-oligomeric complex is the chaperonin GroEL, with a native molecular weight of 850 kDa. When the macromolecular complex is formed by multiple numbers of non-identical subunits, it is referred to as a hetero-oligomeric macromolecular complex. A common example for a hetero-oligomeric complex is the eukaryotic 20S proteasome, with a native molecular weight of 750 kDa. The structural complexity of such macromolecular complexes can range from globular to elongated and fibrillary structures. The upper size limit for macromolecular complexes are presently unknown and structures such as the nuclear pore complex and several viruses are known to exceed 100 MDa in size.

As used herein, the term "osmolyte" refers to compounds affecting osmosis. Examples include but are not restricted to glycerol, sucrose, sugars in general, trimethylamine-N-oxide (TMAO) and ethylene glycol.

The term "polymer with zero net charge" refers to a polymer, which is built up by the consecutive covalent attachment of a repeating chemical unit in the size range of hundreds of Daltons. The definition of zero net charge is satisfied by the properties of the repeating unit, which ideally contains no electronic charge (neither positive nor negative). If electronic charges are present, they should appear in a balanced manner, i.e. positive charges with a value of two should be counter-balanced by negative charges with a value of two. Such molecules with counter-balanced electronic charges are referred to as zwitterionic species or chemicals.

The term "crystal" refers to a supramolecular assembly of any given single molecule or molecular species in a spatially repetitive manner. Hereby, the molecule or molecular species can be defined as any chemical moiety where the atoms are connect by covalent bonds and/or non-covalent bonds. Examples for non-covalent bonds include but are not restricted to hydrogen-bonds, electrostatic interactions and Vander-Waals contacts. The relation of one molecule in a crystal to another can be described by strict symmetry rules, which are based on the Bravais lattices.

The term "comprise" or "comprising" or the term "contain" or "containing" are used herein interchangeably, said terms include the embodiments "consist" or "consisting of".

The term "non-ionic polymer" refers to a molecule, which is built up by the consecutive covalent attachment of a repeating chemical unit in the size range of hundreds of Daltons. When the chemical unit contains no electronic charge, the resulting polymer is referred to as a non-ionic polymer.

The method according to the present invention aims in providing a simple and rapid procedure enabling purification of biological macromolecular complexes. The complexes are provided with high homogeneity, thus, allowing a reproducible crystallization. Further, the chemical conditions enabling the rapid crystallization of the biological macromolecular complex in a reproducible manner and sufficient abundance for screening are provided.

The method aims in providing crystals being of sufficient size to allow for soaking experiments with compound libraries, thus, identifying suitable ligands of said biological macromolecular complexes. This is particularly suitable for application in personal medicine where the personalized drug is determined for treating said individual. Further, this is particularly suitable in case where the first choice drug is not effective in an individual.

These ligands or interactor include compounds interacting with, in particular, altering functionality of the biological macromolecular complexes, including activators, inhibitors and allosteric effectors.

In addition, the method for purification according to the present invention provides purified biological macromolecular compounds suitable for subsequent crystallization, thus, enabling to provide crystals with high stabilization and cryoprotection, hence, enabling diffraction data collection in a resolution range below 2.2 Å, like in the range of 1.8 to 2.2 Å.

The method according to the present invention comprises various steps whereby in an embodiment of the present invention said method allows a chromatography-free purification of the biological macromolecular complexes.

Typically, the biological macromolecular complexes are present in a crude sample, like cells obtained from cell culture or supernatant obtained from cultivation of cells expressing the biological macromolecular complexes.

The crude sample typically consists of a cytosolic extract from cells, e.g. obtained by hypotonic lysis in case of mammalian tissues/cells or freeze grinding, mechanical disruption and/or high pressure rupture in the case of yeasts and fungi as well as prokaryotic expression systems.

In an embodiment, the cell culture is performed in the presence of predetermined components, like cytokines. For example, when the biological macromolecular complexes are immunoproteasomes, cultivation of the cells is conducted with cytokines, in particular interferon gamma, for a time sufficient to induce expression of the immunoproteasome. For example, cell cultivation is for a time ranging of from 48 to 96 hours. The skilled person is well aware of suitable culture conditions for inducing expression of the desired biological macromolecular complexes.

The crude sample is subjected to a first centrifugation step for separation of the cell debris. Said separation step for pelleting cell debris is conducted at 25.000 to 35.000×g to obtain an extract and the supernatant accordingly. For example in case of centrifugation at 30.000×g an S30 extract is obtained. The skilled person is well aware of the term S30 accordingly.

As a next step, the supernatant obtained after the first centrifugation step is treated with compounds allowing thiol-alkylation and/or reduction of cysteines. Namely, the present inventors recognized that thiol-alkylation and/or reduction of cysteines at this time point allows to improve the purification method purifying biological macromolecular complexes. That is, effecting thiol-alkylation and/or reduction of the cysteines at this time point is beneficial for the stability and purity of the biological macromolecular complexes obtained.

Of note, the compounds allowing thiol-alkylation and/or reduction of cysteines may be present in the buffer systems used in the present invention before or after this specific step.

Preferred embodiments of the compounds enabling thiol-alkylation (S-alkylation) of the cysteines include iodoacetamide, iodoacetate, and N-ethylmaleimide, as well as compounds like Dithiothreitol (DTT), Dithioerythritol (DTE), β-Mercaptoethanol (β-ME) or Tris(2-carboxyethyl)phosphin (TCEP).

The S-alkylation and/or thiol cysteine-reducing compound is present in the final solution in an amount of 1 to 100 mM, for example 2 to 50 mM like 5 to 30 mM. For example, two different S-alkylation compounds may be present. In an embodiment, iodacetamide is added in a final concentration of 10 mM in total in combination with N-ethylmaleimide in a final concentration of 10 mM.

Further, an osmolyte may be added to said cytosolic extract obtained from the first centrifugation step. Said osmolyte may be absent or may be present in an amount of 0.5 to 25% (w/v). In an embodiment, 10 to 25% (w/v), like 15 to 20% osmolyte is added. For example, the osmolyte is a sugar, like a disaccharide. Preferred osmolyte include sucrose, glycerol, TMAO, ethylene glycol, propylene glycol, glucose, galactose, maltose, fructose. In an embodiment, sucrose powder is added in an amount to 15 to 25% (w/v) to the solution of supernatant and a purification buffer.

Moreover, a protease inhibitor may be added. For example, benzamidine chloride, a known protease inhibitor, namely a trypsin inhibitor, may be added in an amount of 1 mM to 100 mM, like 5 mM to 20 mM, in particular 10 mM.

In addition, the osmolyte as well as the protease inhibitor, the S-alkylation and/or cysteine-reducing compound may be present in the buffer systems present in the preceding steps or the subsequent steps accordingly. The skilled person can easily determine where these components are required.

In addition, said buffer may further contain a non-ionic detergent, like octyl glucose neopentyl glycol (OGNG) or other suitable detergents including other members of the neopentyl glycol group.

In an embodiment of the present invention, the osmolyte is present and is sucrose.

Treating the supernatant with the mentioned compounds according to step c) of the present invention is conducted preferably at room temperature but may be effected in a range between 4° C. and 25° in a first step for a sufficient time like 10 minutes to 1 hour, e.g. 30 minutes. In some embodiments, incubation is continued at a higher temperature than the first temperature, e.g. between 25° C. and 37° C. with shaking for a sufficient time, e.g. for 50 minutes to 2 hours.

Thereafter, a second centrifugation step is conducted. Said second centrifugation step is conducted by centrifugation at 50.000 to 150.000×g. For example, centrifugation is effected at a range of 80.000×g to 120.000×g. In an embodiment, the centrifugation step results in an S100 extract.

The second centrifugation step is conducted for sufficient time to obtain an extract. For example, centrifugation is conducted for at least 1 hour, like 2 hours at 4° C. The skilled person is well aware of suitable conditions for conducting said centrifugation step.

After centrifugation, a filtration step may be included to clarify the obtained cytoplasmatic extract further. The filtration step may be conducted also in preceding or subsequent steps depending on the crude sample and the biological macromolecular complexes.

The supernatant obtained from the second centrifugation step is then treated with a water-soluble polymer. Suitable water-soluble polymers include non-ionic polymers or a polymer with zero net charge. In an embodiment, preferred polymers include polyalkylene glycol, polyamine or polycarboxylate. Other structures representing suitable polymers for precipitation include various polymeric precipitants. (a) M-type Jeffamines. R1=—H for EO or —CH3 for PO. The PO/EO molar ratio is 29/6 for Jeffamine M2005, 10/31 for Jeffamine M2070 and 9/1 for Jeffamine M600. (b) Pentaerythritol ethoxylate. (c) Pentaerythritol propoxylate. (d) Polyvinyl pyrrolidone. (e) Polypropylene glycol. (f) Polyvinyl alcohol. (g) Polyacrylate. (h) Cellulose-based polymers. R1=—H, —CH3 or —CH2CHOHCH3 (hydroxypropyl methylcellulose), —H or CH2CO2H (carboxymethyl cellulose). (i) Poly(ethylene imine). (j) Di[poly(ethyleneglycol)] adipate. (k) Jeffamine ED2003. (l) Jeffamine D2000. (m) Jeffamine SD2001. (n) T-type Jeffamines. (o) Polyacrylamide. (p) Glycerol ethoxylate. (q) Acrylic acid/maleic acid copolymer. (r) Vinylpyrrolidone/vinylimidazole copolymer. These various polymer precipitants are also shown in scheme 1 below.

Scheme 1

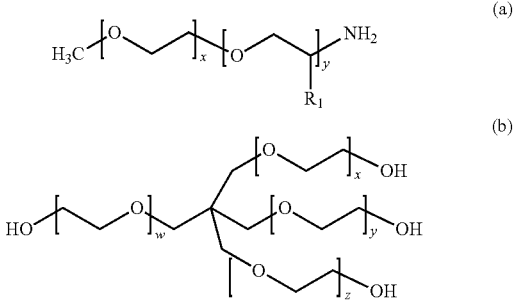

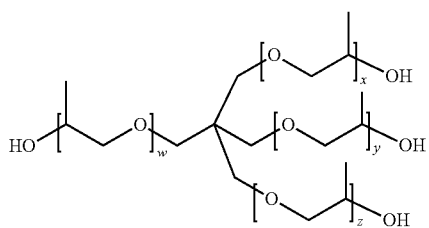
(c)

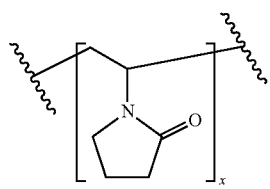
(d)

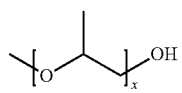
(e)

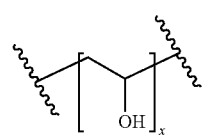
(f)

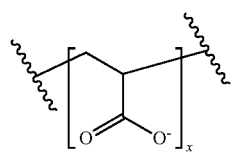
(g)

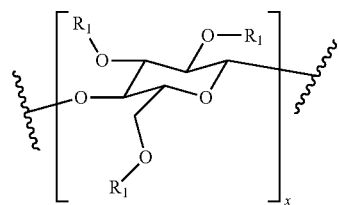
(h)

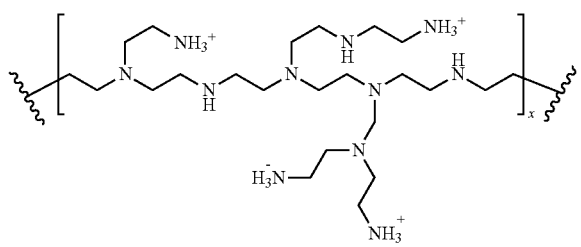
(i)

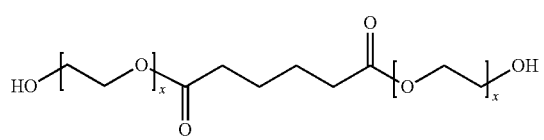
(j)

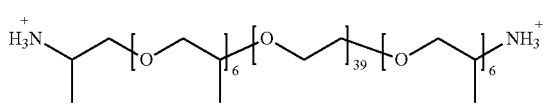
(k)

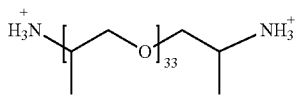
(l)

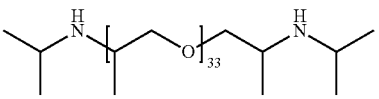
(m)

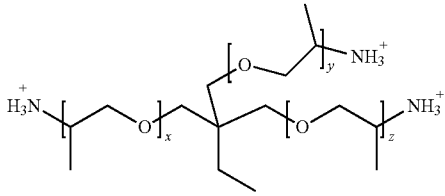
(n)

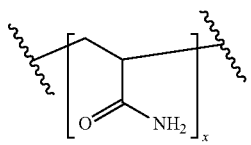
(o)

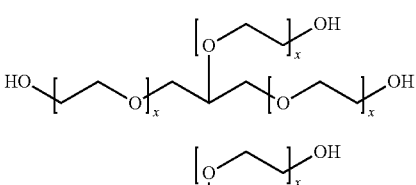
(p)

(q)

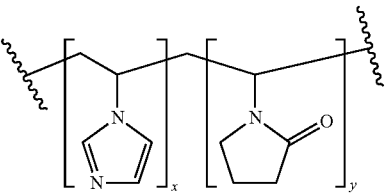

(r)

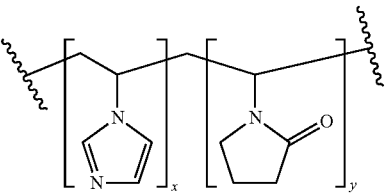

Each of the indices x, y, z and w is independently chosen from the integer numbers 0, 1, 2, 3, 4, 5, 6, 7, 8, 9 and 10.

In an embodiment, the supernatant is treated with a polyalkylene glycol, like polyethylene glycol. Suitable polyalkylene glycol polymers include polyethylene glycol, in particular, polyethylene glycol 400 to 20.000, like 400 to 6000. With respect to the PEG polymers, the number signifies the mean molecular weight of the PEG polymer accordingly.

The supernatant is precipitated with said polymer for example using PEG 400 in a concentration of 20% (w/v) under stirring at 4° C. and incubated thereafter. Incubation time may be about 10 to 30 minutes. That is, the polymer is added in a suitable concentration, typically in the range of 5% to 30% (w/v) like 15% to 25% (w/v) to the extract. The amount of the polymer added depends on the polymer used. The skilled person is well aware of selecting suitable concentrations accordingly. Adding the polymer and stirring is conducted at temperatures below 15° C., like below 10° C., for example in the range of 0° C. to 10° C. for a sufficient time, like 10 to 30 minutes, like 20 minutes.

After precipitation the precipitate may be obtained by a further centrifugation step. The precipitate is resuspended in a buffer not containing the polymer used for precipitation, like a buffer not containing the polyalkylene glycol. Said resuspended material is then subjected to a density gradient centrifugation. The resuspension of the precipitate for example after centrifugation at 30.000×g for 30 minutes at 4° C. is effected in a purification buffer containing saccharide, like sucrose, an non-ionic polymer like lauryl maltose neopentyl glycol (LMNG), a reducing agent like dithiothreitol, thus, reducing the disulfide bonds of proteins but not containing PEG.

The density gradient centrifugation, also named the first density gradient centrifugation with the resuspended material after precipitation is performed by loading the same on an osmolyte based gradient, whereby the osmolyte based gradient is e.g. a sugar gradient, like a sucrose based gradient. The gradient may be a gradient of from 10 to 40% (w/v). For example, the osmolyte gradient is a sucrose based gradient of from 10 to 40% (w/v) sucrose. The skilled person will select a suitable gradient to allow separation of the desired biological macromolecular complexes accordingly. Typically, the gradient is selected in a way that the desired biological macromolecular complex is present in the middle or in the second third of the gradient. The gradient is conducted under suitable conditions, that is, for a sufficient time at e.g. 4° C. with e.g. 270.000×g. Typically, the gradient is a linear gradient but exponential convex or exponential concave gradients are possible.

The gradients are harvested by a known method and the fraction containing the biological macromolecular complexes is precipitated by a water-soluble polymer, typically, the same water-soluble polymer as used before.

If necessary, the precipitation resuspension and the density gradient centrifugation is repeated to arrive at a purified biological macromolecular complex accordingly. After the last density gradient centrifugation, the biological macromolecular complexes are concentrated by water-soluble polymer based precipitation for obtaining the purified biological macromolecular complex.

In an embodiment, the first centrifugation step is a centrifugation to obtain an S30 fraction and/or the second centrifugation step is a centrifugation obtaining an S100 fraction.

Further, the supernatant obtained after the second centrifugation step which may optionally be subject to a filtering, is subjected to a differential precipitation with a water-soluble polymer, in particular, a non-ionic polymer or a polymer with zero net charge, like polyalkylene glycol, polyamine, or polycarboxylate, in particular, a polyethylene glycol, comprising a first precipitation step with a lower concentration of the water-soluble polymer, in particular, a non-ionic polymer or a polymer with zero net charge, like polyalkylene glycol, polyamine, or polycarboxylate whereby the biological macromolecular complexes are maintained in the supernatant and with a further precipitation step with a higher concentration of the water-soluble polymer, in particular, a non-ionic polymer or a polymer with zero net charge, like polyalkylene glycol, polyamine, or polycarboxylate for precipitating the biological macromolecular complexes.

The differential precipitation allows to separate the desired biological macromolecular complexes with less density gradient centrifugation and precipitation steps.

The purification as well as the fractions of the density gradient may be controlled by SDS-page analysis. The skilled person is well aware of suitable methods controlling the purification accordingly.

In an embodiment, the biological macromolecular complex to be purified is a proteasome, like the 20S proteasome or the 26S proteasome including the respective immunoproteasome. In case of purification of the 20S proteasome or the 26S proteasome, the steps of precipitation and density gradient centrifugation are repeated at least once whereby PEG 400 is used as the polymer of choice and the density gradient is a sucrose based linear density gradient of 10 to 30% (w/v) sucrose.

In another embodiment, the biological macromolecular complex is a fatty acid synthase, e.g. a yeast fatty acid synthase. Here the steps of precipitation and density gradient are repeated at least twice, for example three times. In addition, the density gradient is a sucrose based linear density gradient of 10 to 45% (w/v) sucrose. In addition, the S-alkylating and/or cysteine-reducing agent is DTT. The supernatant obtained after the second centrifugation step is subjected to a differential precipitation e.g. using PEG400 with 20% (w/v) PEG400 in the first precipitation step and, thereafter, precipitating the supernatant obtained with 30% (w/v) PEG400 for obtaining a precipitate or pellet accordingly.

As demonstrated in the examples, it is possible to obtain the purified biological macromolecular complexes with the method according to the present invention whereby these complexes have a high purity allowing further crystallization of the complexes.

In a further aspect, the present invention relates to a method for crystallization of biological macromolecular complexes. The method for crystallization according to the present invention comprises the method for the purification of the biological macromolecular complexes as described herein. After purification the purified complexes are resuspended in a reservoir solution containing a water-soluble polymer, in particular, a non-ionic polymer or a polymer with zero net charge, like polyalkylene glycol, polyamine or polycarboxylate, in particular, polyethylene glycol. The reservoir buffer, also known as crystallization buffer, is typically a buffer containing a Tris, HEPES or BisTris buffer system in an amount of 0.1 M. In addition, the water-soluble polymer, e.g. polyethylene glycol like PEG 3350 in case of the 20S proteasome is in the range of 5 to 30 (w/v), like 10 bis 20% (w/v), e.g. 10% (w/v). In the case of FAS, polyethylene glycol like PEG3350 is in the range of 5 to 20% (w/v), e.g. 14% (w/v)

The suitable conditions may be determined using the ProteoPlex method described e.g. in Chari A. et al, Nat. Methods, 2015, 12, 859-865 or in WO 2013/034160. The crystallization may be continued by stabilizing and dehydrating the crystals further allowing reproducible resolution of said crystals below 2 Å. The crystallization method may be conducted with biological macromolecular complexes having a protein concentration of at least 5 mg/ml. In addition, the step of crystallization may be conducted first at a temperature above 15° C. and, thereafter, at a temperature of equal or below 8° C. That is, while in a first step, a controlled stabilization is conducted using a suitable crystal stabilization buffer, like a BisTris buffer as described above with higher amounts of polymer, the dehydration at a lower temperature of the crystal is conducted with a crystal dehydration buffer which is similar to the crystal stabilization buffer but may contain higher amounts of polymer, and, in addition, alcohol like MPD, 2-Methyl-2,4-pentanediol or glycerol.

The buffers mentioned above, namely, the crystallization buffer, the crystal stabilization buffer and the crystal dehydration buffer may contain additionally magnesium chloride, MgCl$_2$. For example in case of the 20S proteasome, magnesium chloride is present in an amount of 0.2 M in the buffers accordingly. In the case of FAS, the crystal dehydration buffer contains either magnesium chloride, potassium iodide, sodium chloride, potassium acetate or potassium chloride in the range of 0.2-5 M.

The presence or absence of magnesium chloride or other salts may depend on the biological macromolecular complexes. As mentioned, using the method described in WO 2013/034160 would allow to identify the suitable conditions accordingly. In an embodiment of the crystallization method according to the present invention, the crystals are soaked further with compounds interacting with the biological macromolecular complexes or supposed to interact with these complexes. For example, the crystals are soaked with activators, inhibitors or other kind of ligands interacting, e.g. binding to the biological macromolecular complexes accordingly. For example, in case of proteasome inhibitors to be included into the proteasome crystals, the proteasome crystals are incubated with a buffer system containing said inhibitors, like the crystal dehydration buffer system mentioned above, further containing the proteasome inhibitor in sufficient amount, e.g. in an amount of 1 to 10 mM.

After incubation for a sufficient time, for example at least 5 hours, like at least 10 hours, the crystals may be harvested thereafter and are ready for analysis.

That is, the method for crystallization of biological macromolecular complexes according to the present invention allows to provide a large number of crystals optionally soaked with a compound interacting therewith. Thus, it is possible to allow for soaking experiments with compound libraries and, eventually, determining the most suitable interactor, like activator or inhibitor or other biological macromolecular complexes influencing compounds. For example, in case of the 20S proteasome or the 26S proteasome including the immunoproteasome, the compound libraries may be composed of candidate compounds for inhibiting the proteasome complex. In case of personalized medicine, the 20S proteasome including the immunoproteasome or any other biological macromolecular complex may be crystallized by the method according to the present invention and, thereafter, candidate compounds are incubated with the crystals, thus, allowing interaction therewith, for determining suitability of said candidate compounds as an interactor of said complexes. For example in case of inhibitors of the 20S proteasome, the most suitable inhibitor for treating an individual is determined. Further, this method is suitable for identifying compounds active as inhibitors of the 20S proteasome in case of individuals being resistant to a first choice inhibitor, like Bortezomib, Carfilzomib, Dihydroeponomicin, Eponomicin, Marizomib, Ixazomib, Delanzomib, ONX-912 (Oprozomib) or ONX-0914.

That is, in another embodiment of the present invention, a method is provided for determining the suitability of a candidate compound for inhibiting the 20S proteasome including the immunoproteasome of an individual. Said method comprises the steps of the steps described in the method for crystallization of a 20S proteasome of said individual containing the candidate compound according to the present invention or, alternatively, providing a crystallized 20S proteasome containing the candidate compound according to the present invention. Typically, the candidate compounds are introduced into the crystals by soaking the same into the crystals as described above.

After incorporation of the candidate compound into the crystallized biological macromolecular complexes exemplified by the 20S proteasome, e.g. by soaking, the crystal structure of the 20S proteasome is determined. For example, the crystal structure is determined by diffraction analysis with a resolution of 2.2 Å or below. Based on the crystal structure of the biological macromolecular complex with the candidate compound, the suitability of said candidate compound is determined. For example, it is determined whether the candidate compound is suitable as an inhibitor for the 20S proteasome of an individual based on the diffraction analysis at 2.2 Å or below.

The method according to the present invention is particularly useful for determining suitable compounds as active drugs for treating said individuals, namely, for applying personalized medicine. For example, where the individual is an individual not responding to a first inhibitor of the 20S proteasome, like Bortezomib, Carfilzomib, Dihydroeponomycin, Eponomicin or ONX-0914.

The candidate compounds, e.g. in form of inhibitors of the 20S proteasome including the immunoproteasome may be used in a method of treating, ameliorating or preventing cancer, an autoimmune disease, muscular dystrophy, emphysema, or cachexia accompanying cancer or AIDS. The cancer may be a cancer selected from lymphoid malignancy, preferably selected from multiple myeloma (MM) including relapsed and refractory MM; non-hodgkin lymphoma such as B-cell lymphomas including mantle cell lymphoma (MCL) and diffuse large B-cell lymphoma (DLBCL), and Waldenström macroglobulinaemia or autoimmune diseases selected from rheumatoid arthritis, systemic lupus erythematosus, Sjörgen's syndrome or scleroderma.

In a further embodiment, the present invention relates to a purified biological macromolecular complex obtainable by a method according to the present invention. These purified biological macromolecular complexes obtainable with the method according to the present invention are characterized in having high homogeneity, thus, being particularly suitable for further crystallization. In addition, the purification method represents a method allowing reproducible and sufficient purification of these biological macromolecular complexes accordingly. The complexes obtained are obtained in high purity and abundance.

As demonstrated, the purification allows to provide crystals of the biological macromolecular complexes allowing diffraction analysis with high resolutions not described before, namely, in a resolution of 2.2 Å and below, like in a resolution range of 1.8 to 2.2 Å.

In an embodiment, the purified biological macromolecular complex is composed of at least two heterologous or homologous proteinaceous subunits or being a combination of the nucleic acid molecules and proteins. The purified biological macromolecular complexes include proteasomes including the immunoproteasome, like 20S proteasome or 26S proteasome as well as Chaperonin complexes, like GroEL, GroEL-ES, Hsp60, Hsp60-10, as well as 40S-, 60S- and 80S-ribosomes, eukaryotic fatty acid synthase, oxoglutarate dehydrogenase and pyruvate dehydrogenase complexes.

Furthermore, the present invention relates to a crystallized biological macromolecular complex obtainable by the crystallization method described herein. These crystallized biological macromolecular complexes allow diffraction analysis with a resolution of 2.2 Å or below. For example in case of the 20S proteasome including the immunoproteasome, it was possible for the first time to allow resolution in the range of from 1.8 to 2.2 Å.

Based on this resolution, it is possible to identify suitable interactors of the biological macromolecular complexes, like the 20S proteasome by soaking said compounds into the crystals and, thereafter, analyzing the same by diffraction analysis with high resolution of 2.2 Å or below. That is, it is possible to identify whether these compounds are present in active sites of the biological macromolecular complexes or whether they are present with other sites influencing activity of these complexes accordingly. The suitability of the method and the purified biological macromolecular complexes as well as the crystallized biological macromolecular complexes is exemplified by the 20S proteasome. However, further data are obtained for Chaperonin complexes, like GroEL, GroEL-ES, eukaryotic Hsp60, eukaryotic Hsp60-10, 40S-, 60S- and 80S-ribosomes and eukaryotic fatty acid synthase.

FIG. 1 is a flowchart of the steps according to the method for purification of biological macromolecular complexes as described above.

The examples given below illustrate the invention further without restricting the invention.

EXAMPLES

Materials and Methods:

Materials

Standard chemicals were obtained from Sigma Aldrich (Taufkirchen, Germany). The proteasome inhibitors Oprozomib, Epoxomicin and Dihydroeponemycin were purchased from ApexBio (Houston, USA), MLN9708 and Bortezomib were obtained from Selleck Chemicals (Munich, Germany) and Z-LLY-Ketoaldehyde from Bachem (Bubendorf, Switzerland), and were resuspended in DMSO at 100 mM concentration. Detergents were obtained from Anatrace (Maumee, USA), crystallization plates from Hampton Research (Aliso Viejo, USA), Litholoops from Molecular Dimensions (Suffolk, UK) and Jena Bioscience (Jena, Germany).

Table S1: Buffers for protein purification, crystallization, crystal stabilization, crystal dehydration and enzymatic assays Purification buffer: 0.05 M BisTris pH 6.5, 0.05 M KCl, 0.01 M MgCl2, 0.01 M β-Glycerophosphate Crystallization buffer: 0.1 M BisTris pH 6.5, 0.2 M MgCl2, 10% (w/v) PEG3350

Crystal stabilization buffer: 0.1 M BisTris pH 6.5, 0.2 M MgCl2, 20% (w/v) PEG 3350

Figure 2:
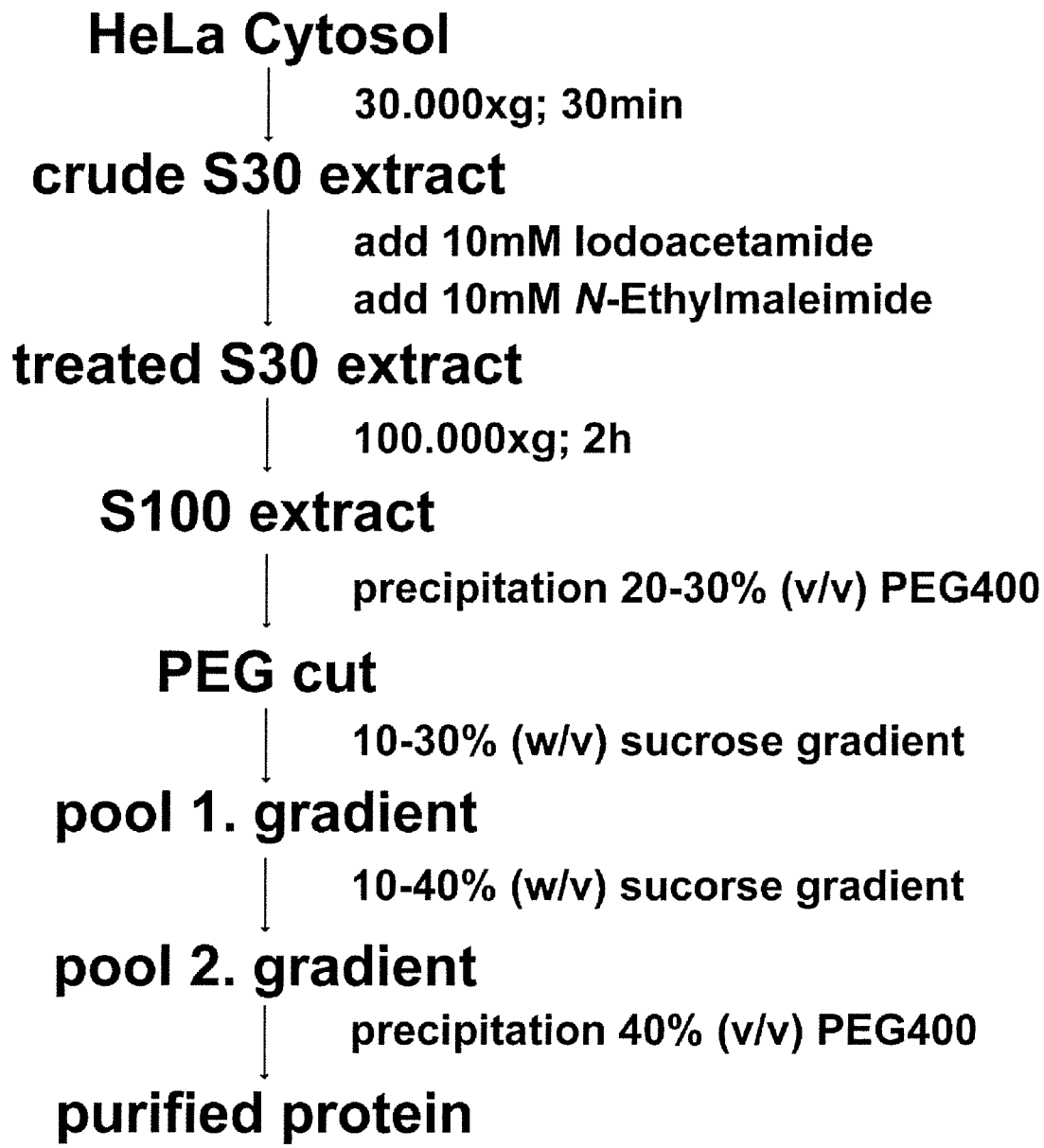
FIG. 2.

Crystal dehydration buffer: 0.1 M BisTris pH 6.5, 0.2 M MgCl2, 25% (w/v) PEG 3350, 20% (v/v) MPD Methods Purification of Human 20S Proteasomes as Depicted in FIG. 2

S30 HeLa cytoplasmic extract was prepared by hypotonic lysis according to Dignam et al. (20), with some minor modifications: after hypotonic lysis and centrifugation to collect nuclei, the supernatant (the crude cytoplasmic extract) was centrifuged at 30,000×g for 30 minutes at 4° C. and flash frozen in 40 ml aliquots in liquid nitrogen and stored at −80° C. until further use. The S30 HeLa cytoplasmic extract was thawed in a water bath at 37° C., supplemented with purification buffer to 1× concentration from a 10× stock, followed by the addition of sucrose powder to 20% (w/v), Octyl Glucose Neopentyl Glycol (OGNG; from a 10% (w/v) stock solution in water) to 0.1% (w/v), Iodacetamide to 10 mM, N-Ethylmaleimide to 10 mM and Benzamidine Chloride to 10 mM. The extract was incubated at room temperature on a magnetic stirrer for 30 minutes, followed by incubation at 30° C. with shaking at 140 rpm for 1 hour. The treated extract was centrifuged at 100,000×g for 2 hours at 4° C. After centrifugation, the supernatant was filtered through 3 layers each of cheese cloth and miracloth to obtain a S100 HeLa cytoplasmic extract.

Figure 3:
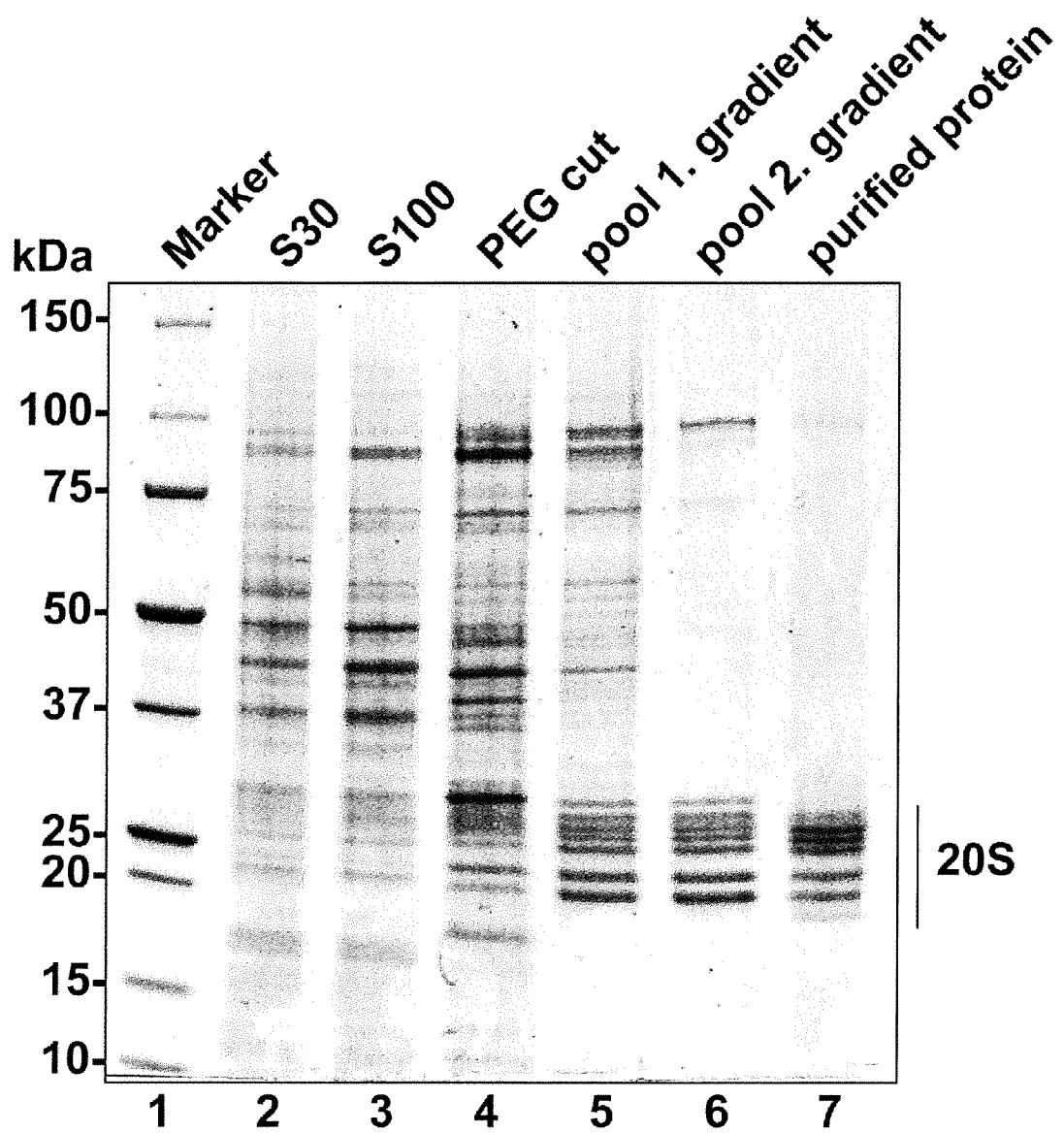
FIG. 3.
Figure 4:
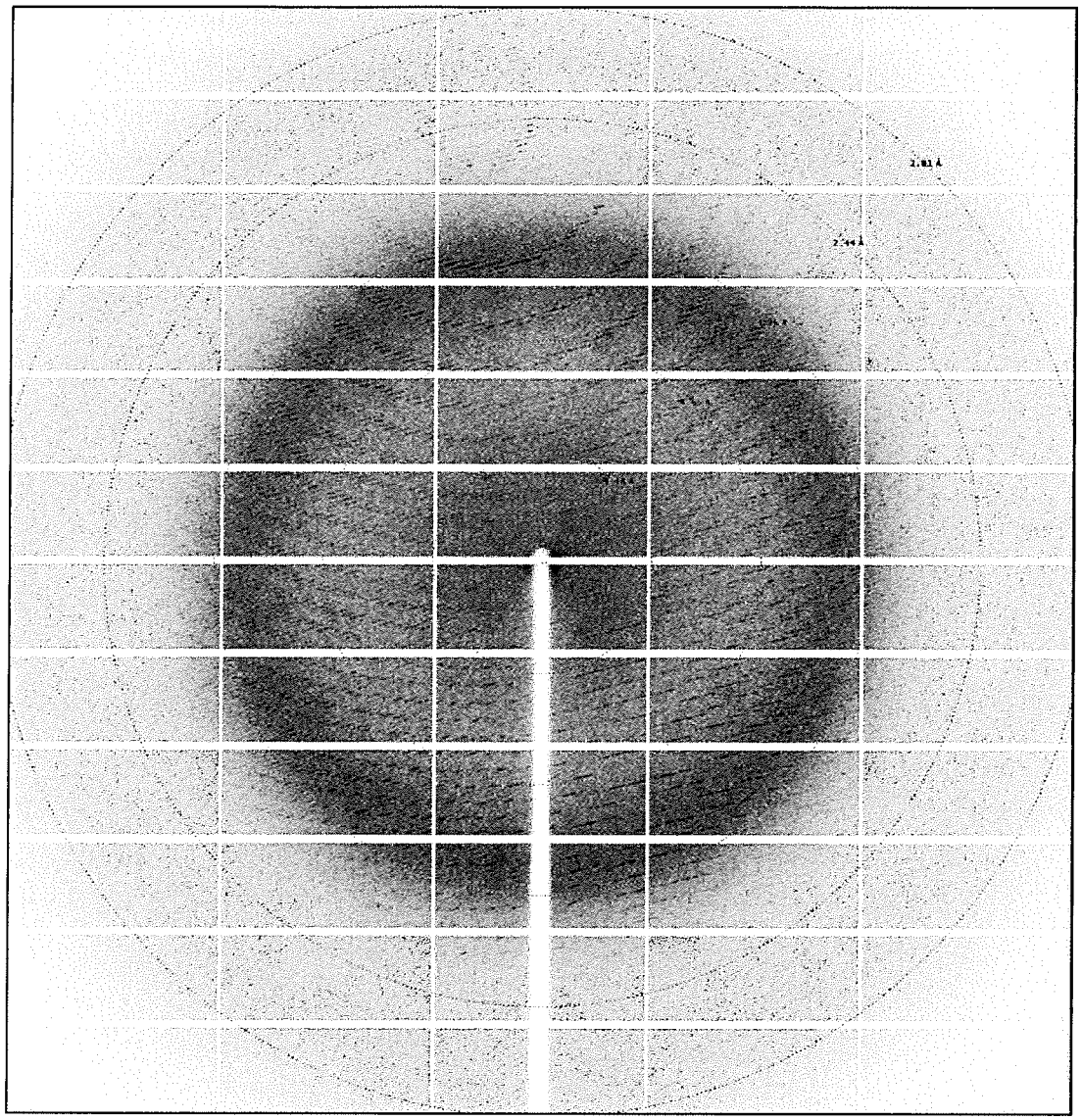
FIG. 4.

The clarified extract is subjected to differential precipitation with PolyEthyleneGlycol400 (PEG; number signifies the mean molecular weight of the PEG polymer). PEG400 is added to a concentration of 20% (v/v) to the S100 HeLa cytoplasmic extract under stirring at 4° C. and incubated for 20 minutes. Precipitated proteins are removed by centrifugation at 30,000×g for 30 minutes at 4° C. The supernatant is then precipitated by raising the concentration of PEG400 to 30% (v/v) as described above. The precipitate of this step, which contains human 20S proteasomes, is recovered by centrifugation at 30000×g for 30 minutes at 4° C. and resuspended in purification buffer containing 2% (w/v) sucrose, 10 mM DTT and 0.01% (w/v) Lauryl Maltose Neopentyl Glycol (LMNG) in an orbital shaker at 18° C. The resuspended material is loaded on 10-30% (w/v) sucrose gradients in purification buffer containing 5 mM DTT, which are centrifuged at 270,000× g for 16 h at 4° C. Gradients were harvested in 400 μl fractions with Äkta Prime (G E Healthcare). SDS-PAGE was utilized to identify fractions containing 20S proteasomes. Selected fractions were pooled and precipitated by the addition of 40% (v/v) PEG400. After centrifugation (30,000×g, 20 minutes), the supernatant was removed and the precipitate was resuspended in Purification buffer containing 5% (w/v) sucrose, 10 mM DTT and 0.01% (w/v) LMNG. The resuspended material is loaded on linear 10-40% (w/v) sucrose gradients in Purification buffer containing 5 mM DTT, which are centrifuged at 284,000×g for 20 h at 4° C. Fractions containing 20S proteasomes are yet again identified by SDS-PAGE, precipitated and concentrated by the addition of 40% PEG400 and resuspended in Purification buffer containing 5% (w/v) sucrose, 5 mM DTT and 0.01% LMNG, yielding the finally purified protein preparation at 13 mg/ml. Protein concentrations were determined by the Bradford assay (Bio-Rad, Munich, Germany) using BSA as a standard. This procedure reproducibly yields 20 mg purified human 20S proteasomes, starting from 300 ml S100 HeLa cytoplasmic extract at a concentration of 10 mg/ml. The entire purification procedure is concluded within 48 hours yielding crystallization grade protein. The purification is demonstrated in FIG. 3 showing an SDS page of fractions from different purification steps.

Crystallization of Human 20S Proteasomes

Human 20S proteasomes are crystallized at a protein concentration of 7.5 mg/ml by mixing 0.5 μl protein+0.5 μl Crystallization buffer in Chryschem sitting drop vapor diffusion plates (Hampton Research, Aliso Viejo, USA) over a 500 μl reservoir of Crystallization buffer. Under these conditions, human 20S proteasomes crystallize in space group P212121 with unit cell constants a=114 Å, b=202 Å, c=302 Å, α=β=γ=90°. The purification procedure described above is therefore suitable to typically perform in excess of 5000 crystallization setups. Additional advantages of the presently identified crystallization conditions include that each crystallization setup typically yields 10-15 crystals, which are 150×150×200 μm3 in size. Crystallization to full size of the crystals is achieved within 20 hours of incubation (see FIG. 1). Hence, ~50000 crystals can be generated within 72 hours of extract preparation that all typically diffract to resolutions below 2 Å.

Crystal Stabilization and Dehydration

Human 20S proteasome crystals obtained by the procedures described above need to be stabilized and dehydrated in a controlled manner to reproducibly diffract to resolutions below 2 Å. We have spent considerable effort to establish reproducible procedures to achieve this. Three steps are involved: 1) Crystallization trays containing human 20S crystals initially grown at 18° C. are placed into Styrofoam boxes and transferred to 4° C. The trays are typically incubated for 8 hours. 2) The crystals are stabilized and dehydrated at 4° C. Initially, seals are removed and 1 µl of reservoir solution is added. Then 2 µl of the Crystal stabilization buffer is added to the crystallization drop. At the same time the reservoir solution is exchanged to Crystal dehydration buffer. The drops are then re-sealed and allowed to equilibrate against the new reservoir solution by vapor diffusion in excess of 8 hours at 4° C. 3) Proteasome inhibitors are soaked into the crystals by the addition of 4 µl of Crystal dehydration buffer to the drops, which additionally contains 5 mM of the proteasome inhibitor of choice (final concentration: 2.5 mM). The drops are then resealed and allowed to equilibrate in excess of 12 hours. The entire crystal stabilization, dehydration and ligand soaking procedures are therefore concluded within 30 hours.

Purification of Human 20S Immunoproteasomes.

Similar to the method described above regarding purification of human 20S proteasomes, the immunoproteasomes are purified following the same approach whereby the crude sample provided is obtained from cell culture cultivated with 200 U/µl interferon gamma for 72 hours, as described in the art.

The crystallization of the immunoproteasome was effected as described above. It was possible to obtain resolutions below 2.2 Å.

Purification of Yeast Fatty Acid Synthase (FAS)

In short, the purification of yeast Fas is conducted as follows:

1) 770 g of grinded yeast cells S. cerevisiae or C. thermophilum) were thawed with stirrer at 37 deg for 30 min.

2) Add
(168 ml×2) of 1× Standard buffer (SB) (acetate).
5 mM PMSF (solution)
10 mM Benzamidine
10 mM Beta-glycerophosphate
20 mM DTT
20% (w/v) Sucrose 3) Incubate for 30 mins at RT.

4) Centrifuge at 30000 g for 30 mins and filter the supernatant using mira and cheese cloth (3 layers each)

5) Add 0.2% OGNG (solution) to supernatant and incubate at 30 deg for 1 h.

6) Centrifuge for 1 h 37 krpm (Ti45Beckmann-Coulter).

7) Filtrate the supernatant using 3 layers of mira and cheese cloth.

8) Precipitate with 20% PEG400 in 1×SB (acetate) for 30 min at 18 deg and centrifuge at 27.500 g for 25 mins.

9) Discard the pellet and precipitate the supernatant with 30% PEG 400 in 1×SB (acetate) for 30 min at 18 deg and centrifuge at 27.500 g for 25 mins.

10) Keep the PELLET and discard the supernatant.

11) Resuspend the Pellet in resuspension buffer (2% sucrose, 1×SB acetate buffer, 10 mM DTT, 10 mM beta-gal, 0.01% LMNG) (Lauroylmaltosideneopentylglycol).

12) Load the resuspended pellet on 6 vials having SW30 10-45% gradients and run at 30,000 rpm for 16 hrs. (Gradients contain Sucrose, 1× SB acetate buffer, 10 mM DTT and 10 mM Beta-glycerophosphate.)

13) FAS fractions) were pooled, filtered and precipitated using 40% PEG 400 in SB acetate buffer for 1 h at 18 deg. They were centrifuged at 27.500 g for 1 h.

14) The Pellet was resuspended in resuspension buffer (2% sucrose, 1×SB acetate buffer, 10 mM DTT, 10 mM beta-gal, 0.01% LMNG).

15) The resuspended pellet was loaded onto 12 vials Sw40 10-45% gradients and run at 25000 rpm for 16 h.

16) FAS fractions were pooled, filtered and precipitated using 40% PEG 400 in SB acetate buffer for 1 h at 18 deg. They were centrifuged at 27.500 g for 25 min.

17) The Pellet was resuspended in resuspension buffer (2% sucrose, 1×SB acetate buffer, 10 mM DTT, 0.01% LMNG) in a volume of ~4.2 ml.

18) The resuspended pellet was loaded onto 12× Sw40 10-45% gradients and run at 22000 rpm for 16 h.

19) FAS fractions were pooled and precipitated using 40% PEG 400 in SB acetate buffer for 1 h at 18 deg. They were centrifuged at 27.500 g for 25 min.

20) The pellet was resuspended resuspension buffer (20% sucrose, 1×SB acetate buffer, 10 mM DTT, 0.01% LMNG). The final concentration was 15 mg/ml for 1.1 ml.

Starting with 260 g cells, the yield is about 16 mg of yeast fatty acid synthase. The FAS was crystallized following the method described herein and refraction is possible in a range of below 4 Å, in particular at 2.8 Å. In addition, electron-microscopy was conducted with a resolution under 3 Å.

The invention claimed is:

1. A method for determining the suitability of a candidate compound for inhibiting the 20S proteasome of an individual comprising:
   obtaining purified biological macromolecular complexes by
      a) providing a crude sample containing the biological macromolecular complexes;
      b) conducting a first centrifugation step for separation of cell debris at 25.000 to 35.000×g;
      c) supplementing the supernatant obtained from the first centrifugation step with an osmolyte in an amount of from 0% to 25% (w/v) and compounds allowing thiol-alkylation of cysteines;
      d) conducting a second centrifugation step by centrifugation at 50.000 to 150.000×g;
      e) treating the supernatant obtained from the second centrifugation step with a water-soluble polymer for precipitation;
      f) conducting a density gradient centrifugation using the osmolyte with a polymer-based precipitate, after resuspension thereof in a buffer not containing said water-soluble polymer;
      g) optionally repeating once or multiple times steps e) and f); and
      h) concentration by water-soluble polymer based precipitation of the biological macromolecular complexes for obtaining purified biological macromolecular complexes;
   crystallization of the purified biological macromolecular complexes in a reservoir solution containing a water-soluble polymer wherein the water-soluble polymer in the reservoir solution may be the same or different as the water-soluble polymer used in the treating step; and
   determining a crystal structure of a crystallized biological macromolecular complex wherein the crystallized biological macromolecular complex is a 20S proteasome, wherein determining is performed by diffraction analysis with resolution of 2.2 Å or below; and
   determining suitability of the candidate compound as an inhibitor of the 20S proteasome of an individual based on said analysis.

2. The method according to claim 1 wherein a protein concentration of the purified biological macromolecular complexes in the reservoir solution is at least 5 mg/ml for crystallization.

3. The method according to claim 1 wherein the step of crystallization is first at a temperature above 15° C. and, thereafter, at a temperature of equal or below 8° C.

4. The method according to claim 1 further comprising stabilization and dehydration of the crystal at a temperature equal to or below 8° C.

5. The method according to claim 1 wherein the individual is an individual not responding to a first inhibitor of the 20S proteasome.

6. The method of claim 5 wherein the first inhibitor is selected from the group consisting of bortezomib, carfilzomib, dihydroeponemycin, eponomycin, marizomib, ixazomib, delanzomib, ONX-912, and ONX-0914.

* * * * *